United States Patent [19]

Thiele

[11] 4,317,673
[45] Mar. 2, 1982

[54] SYNERGISTIC HERBICIDAL COMPOSITIONS

[75] Inventor: Gerald H. Thiele, Sunnyvale, Calif.

[73] Assignee: Stauffer Chemical Company, Westport, Conn.

[21] Appl. No.: 138,386

[22] Filed: Apr. 8, 1980

Related U.S. Application Data

[63] Continuation-in-part of Ser. No. 69,471, Aug. 24, 1979, abandoned.

[51] Int. Cl.³ .................. A01N 43/36; A01N 47/30
[52] U.S. Cl. .................................. 71/95; 71/118; 71/120
[58] Field of Search .................. 71/95, 120

[56] References Cited

U.S. PATENT DOCUMENTS

| | | | |
|---|---|---|---|
| 3,060,235 | 10/1962 | Martin et al. | 71/120 |
| 3,958,977 | 5/1966 | Prochaska et al. | 71/103 |
| 4,110,105 | 8/1978 | Teach | 71/95 |
| 4,132,713 | 1/1979 | Broadhurst | 71/95 |
| 4,160,659 | 7/1979 | Rodebush et al. | 71/95 |

OTHER PUBLICATIONS

Roberts et al, "Trees and Shrubs etc."; (1972) CA 85, No. 73295q, (1976).
Ishikawa et al, "Cyclohexanedione etc."; (1977), CA 88, No. 17328c, (1978).
Lay et al, "Evaluation of Herbicides, etc."; (1972), CA 76, No. 109107k, (1972).
Ashley, "Evaluation of Several Herbicides, etc."; (1972), CA 76, No. 109094d, (1972).

Primary Examiner—Glennon H. Hollrah
Attorney, Agent, or Firm—M. Henry Heines; Veronica Colby Devitt

[57] ABSTRACT

Synergistic herbicidal activity is displayed by a composition comprising the following two components:

(a) a pyrrolidone of the formula

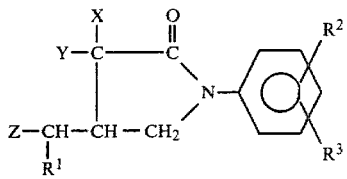

in which X is selected from the group consisting of hydrogen, chlorine and methyl; Y is selected from the group consisting of hydrogen, chlorine and bromine; Z is selected from the group consisting of chlorine and bromine; $R^1$ is selected from the group consisting of hydrogen and $C_1$–$C_4$ alkyl; $R^2$ is selected from the group consisting of hydrogen, $C_1$–$C_4$ alkyl, acetyl, trifluoromethyl, nitro, cyano, $C_1$–$C_4$ alkoxy, $C_1$–$C_4$ alkylthio, $C_1$–$C_4$ alkylsulfonyl, $C_1$–$C_4$ alkylsulfinyl, trifluoromethylthio, trifluoromethylsulfinyl, trifluoromethylsulfonyl, pentafluoropropionamido, and 3-methylureido; and $R^3$ is selected from the group consisting of hydrogen, $C_1$–$C_4$ alkyl, chlorine and trifluoromethyl; and (b) a urea of the formula

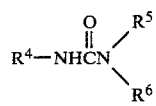

in which $R^4$ is selected from the group consisting of phenyl and substituted phenyl, wherein the substituents are selected from the group consisting of p-chlorophenoxy and alkylacetamido; $R^5$ is selected from the group consisting of hydrogen and $C_1$–$C_4$ alkyl; and $R^6$ is selected from the group consisting of $C_1$–$C_4$ alkyl and $C_1$–$C_4$ alkoxy;

at a weight ratio of (a) to (b) of from about 0.01:1 to about 20:1.

6 Claims, No Drawings

SYNERGISTIC HERBICIDAL COMPOSITIONS

CROSS REFERENCE TO RELATED APPLICATIONS

This is a continuation-in-part of application Ser. No. 069,471, filed Aug. 24, 1979 now abandoned.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, active herbicides have been shown to be more effective in combination than when applied individually. The result is often termed "synergism" since the combination demonstrates a potency or activity level exceeding that which it would be expected to have, based on a knowledge of the individual potencies of the components. The present invention resides in the discovery that certain substituted ureas and certain pyrrolidones, already known individually for their herbicidal potency, display this synergistic effect when applied in combination.

PRIOR ART

The two classes of compounds forming the combination which is the subject of the present invention are independently known in the art for their effects on plant growth. Pyrrolidones are disclosed as herbicides in U.S. Pat. No. 4,110,105 (Teach, Aug. 29, 1979), and substituted ureas of the type included in the present composition (as shown below) are disclosed as herbicides and plant growth regulators in U.S. Pat. Nos. 3,060,235 (Martin et al., Oct. 23, 1962), 3,119,182 (Martin et al., Jan. 28, 1964), and 3,816,498 (Teach, June 11, 1974).

DESCRIPTION OF THE INVENTION

It has now been discovered that synergism in the control of undesirable vegetation is exhibited by compositions comprising a mixture of the following two components:

(a) a pyrrolidone of the formula

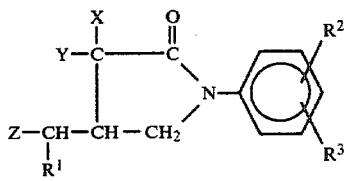

in which

X is selected from the group consisting of hydrogen, chlorine and methyl;

Y is selected from the group consisting of hydrogen, chlorine and bromine;

Z is selected from the group consisting of chlorine and $C_1$–$C_4$ alkyl;

$R^1$ is selected from the group consisting of hydrogen and $C_1$–$C_4$ alkyl;

$R^2$ is selected from the group consisting of hydrogen, halogen, $C_1$–$C_4$ alkyl, acetyl, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido, and 3-methylureido; and $R^3$ is selected from the group consisting of hydrogen, $C_1$–$C_4$ alkyl, chlorine and trifluoromethyl; and (b) a urea of the formula

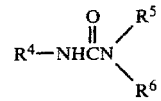

in which $R^4$ is selected from the group consisting of phenyl and substituted phenyl, wherein the substituents are selected from the group consisting of p-chlorophenoxy and alkylacetamido;

$R^5$ is selected from the group consisting of hydrogen and $C_1$–$C_4$ alkyl; and $R^6$ is selected from the group consisting of $C_1$–$C_4$ alkyl and $C_1$–$C_4$ alkoxy.

The terms "alkyl," "alkoxy," "alkylthio," etc., as used herein include both straight-chain and branched-chain groups. All carbon atoms ranges are inclusive of upper and lower limits.

Examples of pyrrolidones useful in the present invention are:

1-phenyl-3-chloro-4-chloromethyl-2-pyrrolidone
1-phenyl-3,3-dichloro-4-chloromethyl-2-pyrrolidone
1-(2',6'-dimethylphenyl)-3-chloro-4-chloromethyl-2-pyrrolidone
1-m-chlorophenyl-3-chloro-4-chloromethyl-2-pyrrolidone
1-p-chlorophenyl-3-chloro-4-chloromethyl-2-pyrrolidone
1-m-trifluoromethylphenyl-3-chloro-4-chloromethyl-2-pyrrolidone
1-phenyl-3-chloro-3-methyl-4-chloromethyl-2-pyrrolidone
1-(3',4'-dichlorophenyl)-3,3-dichloro-4-chloromethyl-2-pyrrolidone
1-m-trifluoromethylphenyl-3,3-dichloro-4-chloromethyl-2-pyrrolidone
1-m-trifluoromethylphenyl-3-chloro-4-methyl-4-chloromethyl-2-pyrrolidone
1-p-tolyl-3-chloro-4-chloromethyl-2-pyrrolidone
1-m-fluorophenyl-3-chloro-4-chloromethyl-2-pyrrolidone
1-m-trifluoromethyl-3-bromo-4-bromomethyl-2-pyrrolidone
1-(3',4'-dichlorophenyl)-3-chloro-4-chloromethyl-2-pyrrolidone
1-m-pentafluoropropionamidophenyl-3-chloro-4-chloromethyl-2-pyrrolidone
cis-1-m-trifluoromethylphenyl-3-chloro-4-chloromethyl-2-pyrrolidone
trans-1-m-trifluoromethylphenyl-3-chloro-4-chloromethyl-2-pyrrolidone
1-m-nitrophenyl-3-chloro-4-chloromethyl-2-pyrrolidone
1-(3',5'-dichlorophenyl)-3-chloro-4-chloromethyl-2-pyrrolidone
1-m-trifluoromethylphenyl-3-chloro-4-(1'-chloroethyl)-2-pyrrolidone
1-m-cyanophenyl-3-chloro-4-chloromethyl-2-pyrrolidone 1-(3',5'-dichlorophenyl)-3,3-dichloro-4-chloromethyl-2-pyrrolidone 1-m-trifluoromethylphenyl-3,3-dichloro-4-(1'-chloroethyl)-2-pyrrolidone 1-m-cyanopenyl-3,3-dichloro-4-chloromethyl-2-pyrrolidone 1-(3'-trifluoromethyl-4'-chlorophenyl)-3-chloro-4-chloromethyl-2-pyrrolidone 1-(3'-trifluoromethyl-4'-chlorophenyl)-3,3-dichloro-4-chloromethyl-2-pyrrolidone 1-m-trifluoromethylthiophenyl-3-chloro-4-chloromethyl-2-pyrrolidone 1-m-methylthiophenyl-3-chloro-4-chloromethyl-2-pyrrolidone 1-m-trifluoromethylsulfinylphenyl-3-chloro-4-chloromethyl-2-pyrrolidone 1-m-methylsulfinylphenyl-3-chloro-4-chloromethyl-2-pyrrolidone 1-m-methylsulfonylphenyl-3-chloro-4-chloromethyl-2-pyrrolidone 1-m-trifluoromethylsulfonylphenyl-3-chloro-4-chloromethyl-2-pyrrolidone 1-(3',5'-bis-trifluoromethylphenyl)-3-chloro-4-chloromethyl-2-pyrrolidone 1-m-methoxyphenyl-3-chloro-4-chloromethyl-2-pyrrolidone 1-m-acetylphenyl-3-chloro-4-chloromethyl-2-pyrrolidone 1-m-tolyl-3-chloro-4-chloromethyl-2-pyrrolidone 1-m-trifluoromethylphenyl-4-chloromethyl-2-pyrrolidone 1-m-bromophenyl-3-chloro-4-chloromethyl-2-pyrrolidone 1-o-chlorophenyl-3-chloro-4-chloromethyl-2-pyrrolidone 1-m-iodophenyl-3-chloro-4-chloromethyl-2-pyrrolidone 1-p-methoxyphenyl-3-chloro-4-chloromethyl-2-pyrrolidone 1-o-trifluoromethylphenyl-3-chloro-4-chloromethyl-2-pyrrolidone.

These and other pyrrolidones within the scope of the invention can be prepared by the procedures described in U.S. Pat. No. 4,110,105.

In the compositions of the present invention, pyrrolidones of the following formula are preferred:

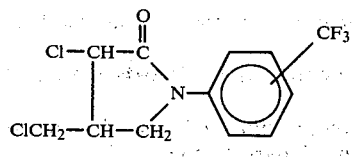

Preferred ureas are the following:
(a) 3-[p-(p-chlorophenoxy)phenyl]-1,1-dimethylurea

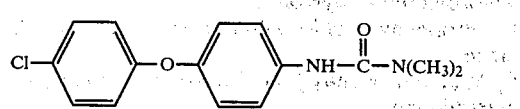

and
(b) 1-(m-t-butylacetamidophenyl)-3-methyl-3-methoxyurea

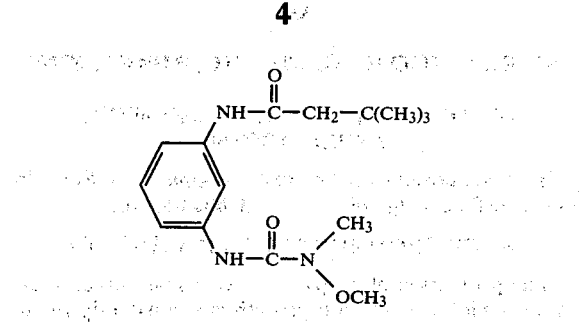

These and other ureas within the scope of the invention can be prepared by the procedures described in U.S. Pat. Nos. 3,060,235, 3,119,182, and 3,816,498.

The terms "synergism" and "synergistic" are used herein to convey the result observed when a combination of herbicides demonstrates a potency in excess of that which the combination would be expected to produce on the basis of the potencies of each herbicide applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example: killing, retardation, stimulating, leaf burn, dwarfing and the like. The term "plants" is used to include germinating seeds, emerging seedlings, and established vegetation, including roots and aboveground portions.

In the compositions of this invention, the pyrrolidone:urea weight ratio at which the herbicidal response is synergistic lies within the range of about 0.01:1 to about 10:1, preferably about 0.1:1 to about 8:1, most preferably about 0.1:1 to about 5:1.

Application rates will depend upon the weeds to be controlled and the degree of control desired. In general, the compositions of this invention are most efficiently employed at a rate of 0.01 to 50 pounds per acre (0.011 to 56 kilograms per hectare) of the active ingredients, preferably 0.1 to 25 pounds per acre (0.11 to 28 kilograms per hectare).

The following examples provide further illustrations demonstrating the synergistic herbicidal response of the present compositions.

EXAMPLE I

This example demonstrates the synergistic response of 1-m-trifluoromethylphenyl-3-chloro-4-chloromethyl-2-pyrrolidone and 3-[p-(p-chlorophenoxy)phenyl]-1,1-dimethylurea in combined pre-emergence application to a variety of weeds.

Fiber planting flats measuring 14.6×25.4×7.0 cm were filled to a depth of 5.0 cm with loamy sand soil, containing 50 parts per million (ppm) each of the commercial fungicide cis-N[(trichloromethyl)thio]-4-cyclohexene-1,2-dicarboximide (Captan ®) and 18-18-18 fertilizer (percentages of N-P$_2$O$_5$-K$_2$O) on a weight basis). Several rows were impressed across the width of each flat and each row was seeded with a single weed species. The weed species included johnsongrass (Sorghum halepense), annual ryegrass (Lolium multiflorum), annual morning glory (Ipomoea purpurea), wild oat (Avena fatua), yellow nutsedge (Cyperus esculentus), jimsonweed (Datura stramonium), and velvetleaf (*Abutilon theophrasti*). Ample seeds were planted to give about 20 to 50 seedlings per row after emergence depending on the size of the plants.

Immediately after seeding, the flats were sprayed with aqueous solutions of the test compounds. The quantities sprayed were such that the amount of each test compound applied per flat corresponded to the desired application rate in pounds per acre. In control flats, the test compounds were applied alone at various application rates, whereas in the test flats, solutions containing both compounds were applied. Additional flats not treated at all were used as standards for measuring the extent of weed control occurring in the treated flats. All flats were then placed in a greenhouse where they were watered regularly.

Two months later, the control and test flats were compared to the standards and the grown weed plants in each row were rated visually in terms of percent control ranging from 0% to 100%, with 0% representing the same degree of growth as the same row in the standard and 100% representing complete kill of all weeds in the row. All types of plant injury were taken into consideration.

The results of these tests are listed in Table I in the columns headed by the symbol "O" (indicating the "observed" results). These results are compared with the expected results, shown in the columns headed by the symbol "E", derived from the control data using Limpel's formula (Limpel et al., 1962, "Weed Control by Dimethylchloroterephthalate Alone and in Certain Combinations," Proc. NEWCC., Vol. 16, pp. 48–53):

$$E = X + Y - XY/100$$

where

X = observed percent injury when one of the herbicides is used alone, and

Y = observed percent injury when the other herbicide is used alone.

An asterisk (*) is used to indicate the tests where the results show synergism, i.e., where the observed result exceeds the expected result. It is clear from the table that synergism was observed at many of the application rates tested.

TABLE I

HERBICIDE SYNERGISM TEST RESULTS

Test Compounds:

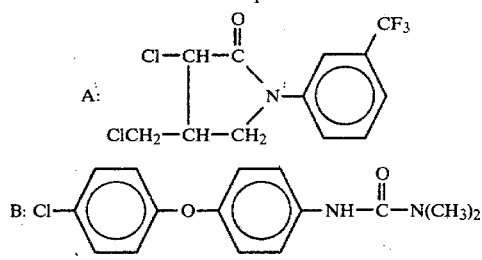

Applied to pre-emergent weeds
Percent Control - O: Observed E: Expected

| Application Rates (lb/A) | | Johnson-grass | | Ryegrass | | Morning glory | | Wild Oat | | Nutsedge | | Jimson weed | | Velvet-leaf | |
|---|---|---|---|---|---|---|---|---|---|---|---|---|---|---|---|
| A | B | O | E | O | E | O | E | O | E | O | E | O | E | O | E |
| *Control Data:* | | | | | | | | | | | | | | | | |
| 0.125 | — | 40 | | 0 | | 0 | | 0 | | 0 | | 30 | | 50 | |
| 0.25 | — | 90 | | 50 | | 0 | | 0 | | 0 | | 90 | | 100 | |
| 0.5 | — | 100 | | 100 | | 50 | | 75 | | 0 | | 95 | | 100 | |
| — | 0.05 | 0 | | 0 | | 0 | | 0 | | 0 | | 0 | | 0 | |
| — | 0.125 | 0 | | 0 | | 0 | | 0 | | 0 | | 0 | | 0 | |
| — | 0.25 | 0 | | 0 | | 0 | | 0 | | 0 | | 0 | | 0 | |
| *Test Data:* | | | | | | | | | | | | | | | | |
| 0.125 | 0.05 | 10 | 40 | 0 | 0 | 0 | 0 | 0 | 0 | 0 | 0 | 30 | 30 | 60* | 50 |
| 0.125 | 0.125 | 20 | 40 | 0 | 0 | 0 | 0 | 0 | 0 | 0 | 0 | 60* | 30 | 100* | 50 |
| 0.125 | 0.25 | 10 | 40 | 0 | 0 | 0 | 0 | 0 | 0 | 0 | 0 | 65* | 30 | 60* | 30 |
| 0.25 | 0.05 | 50 | 90 | 10 | 50 | 0 | 0 | 0 | 0 | 0 | 0 | 75 | 90 | | |
| 0.25 | 0.125 | 100* | 90 | 60* | 50 | 10* | 0 | 0 | 0 | 0 | 0 | 100* | 90 | | |
| 0.25 | 0.25 | 100* | 90 | 80* | 50 | 10* | 0 | 0 | 0 | 0 | 0 | 80 | 90 | | |
| 0.5 | 0.05 | | | 75 | 100 | 0 | 50 | 30 | 75 | 0 | 0 | 100* | 95 | | |
| 0.5 | 0.125 | | | | | 10 | 50 | 40 | 75 | 10* | 0 | 100* | 95 | | |
| 0.5 | 0.25 | | | | | 15 | 50 | 65 | 75 | 10* | 0 | 100* | 95 | | |

*Synergistic effect shown.
Blank spaces indicate 100% control in both observed and expected results, precluding evaluation of synergism.

EXAMPLE II

This example represents a repeat of the test shown in Example I, except that the herbicides were applied to postemergent weeds two weeks after seeding rather than the soil itself on the day of seeding. Injury ratings were taken two months after seeding as before and the results are shown in Table II, where abundant synergism is evident.

TABLE II

HERBICIDE SYNERGISM TEST RESULTS

Test Compounds:

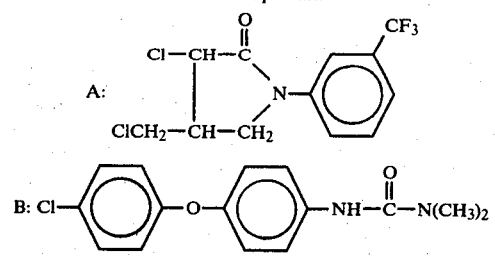

Applied to Postemergent weeds
Percent Control - O: Observed  E: Expected

| Application Rates (lb/A) | | Johnson-grass | | Ryegrass | | Morning glory | | Wild Oat | | Nutsedge | | Jimson weed | | Velvet-leaf | |
|---|---|---|---|---|---|---|---|---|---|---|---|---|---|---|---|
| A | B | O | E | O | E | O | E | O | E | O | E | O | E | O | E |
| Control Data: | | | | | | | | | | | | | | | |
| 0.125 | — | 0 | | 0 | | 0 | | 0 | | 0 | | 70 | | 80 | |
| 0.25 | — | 0 | | 0 | | 0 | | 0 | | 0 | | 75 | | 70 | |
| 0.5 | — | 30 | | 0 | | 0 | | 40 | | 100 | | 100 | | 85 | |
| — | 0.05 | 0 | | 0 | | 0 | | 0 | | 0 | | 0 | | 0 | |
| — | 0.125 | 0 | | 0 | | 0 | | 0 | | 0 | | 0 | | 0 | |
| — | 0.25 | 0 | | 0 | | 0 | | 0 | | 0 | | 0 | | 0 | |
| Test Data: | | | | | | | | | | | | | | | |
| 0.125 | 0.05 | 0 | 0 | 0 | 0 | 60* | 0 | 0 | 0 | 0 | 0 | 100* | 70 | 100* | 80 |
| 0.125 | 0.125 | 10* | 0 | 0 | 0 | 85* | 0 | 0 | 0 | 0 | 0 | 100* | 70 | 100* | 80 |
| 0.125 | 0.25 | 30* | 0 | 0 | 0 | 100* | 0 | 0 | 0 | 0 | 0 | 100* | 70 | 100* | 80 |
| 0.25 | 0.05 | 10* | 0 | 0 | 0 | 100* | 0 | 0 | 0 | 0 | 0 | 100* | 75 | 100* | 70 |
| 0.25 | 0.125 | 20* | 0 | 0 | 0 | 100* | 0 | 0 | 0 | 0 | 0 | 100* | 75 | 100* | 70 |
| 0.25 | 0.25 | 30* | 0 | 0 | 0 | 100* | 0 | 0 | 0 | 0 | 0 | 100* | 75 | 100* | 70 |
| 0.5 | 0.05 | 65* | 30 | 40* | 0 | 100* | 0 | 100* | 40 | 100* | 0 | | | 100* | 85 |
| 0.5 | 0.125 | 95* | 30 | 100* | 0 | 100* | 0 | 100* | 40 | 40* | 0 | | | 100* | 85 |
| 0.5 | 0.25 | 100* | 30 | 85* | 0 | 100* | 0 | 100* | 40 | 30* | 0 | | | 100* | 85 |

*Synergistic effect shown.
Blank spaces indicate 100% control in both observed and expected results, precluding evaluation of synergism.

EXAMPLE III

This example demonstrates the synergistic herbicidal response of 1-m-trifluoromethylphenyl-3-chloro-4-chloromethyl-2-pyrrolidone and 1-(m-t-butylacetamidophenyl)-3-methyl-3-methoxyurea in preemergence application on the day of seeding.

In a procedure similar to Example I, metal flats measuring 21.0×31.1×8.9 cm were used, with the following weed species: wild oat (*Avena fatua*), annual ryegrass (*Lolium multiflorum*), annual morning glory (*Ipomoea purpurea*), prickly sida (*Sisa spinosa*), velvetleaf (*Abutilon theophrasti*), yellow nutsedge (*Cyperus esculentus*), and shattercane (*Sorghum bicolor*). The flats were sprayed on the day of seeding, and injury ratings were taken three weeks later. The results are shown in Table III, where synergism is evident.

TABLE III

HERBICIDE SYNERGISM TEST RESULTS

Test Compounds:

A: 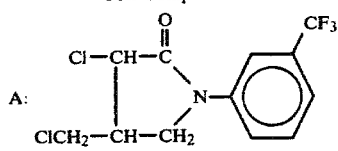

B: 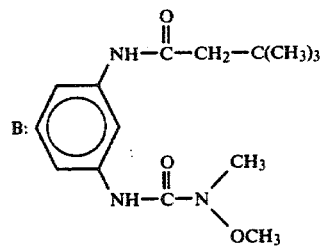

Applied to Soil on day of Seeding
Percent Control - O: Observed  E: Expected

| Application Rates (lb/A) | | Wild Oat | | Ryegrass | | Morning-glory | | Prickly sida | | Velvet-leaf | | Nutsedge | | Shatter-cane | |
|---|---|---|---|---|---|---|---|---|---|---|---|---|---|---|---|
| A | B | O | E | O | E | O | E | O | E | O | E | O | E | O | E |
| Control Data: | | | | | | | | | | | | | | | |
| 0.062 | — | 0 | | 20 | | 0 | | 10 | | 0 | | 0 | | 0 | |
| 0.125 | — | 20 | | 40 | | 30 | | 30 | | 0 | | 0 | | 0 | |
| 0.25 | — | 65 | | 65 | | 40 | | 60 | | 0 | | 65 | | 60 | |
| — | 0.03 | 0 | | 0 | | 0 | | 0 | | 0 | | 0 | | 0 | |
| — | 0.062 | 0 | | 0 | | 0 | | 0 | | 0 | | 0 | | 0 | |
| — | 0.125 | 0 | | 0 | | 0 | | 0 | | 0 | | 0 | | 0 | |
| Test Data: | | | | | | | | | | | | | | | |
| 0.062 | 0.03 | 30* | 0 | 40* | 20 | 0 | 0 | 0 | 10 | 40* | 0 | 0 | 0 | 0 | 0 |
| 0.062 | 0.062 | 40* | 0 | 45* | 20 | 0 | 0 | 0 | 10 | 50* | 0 | 0 | 0 | 0 | 0 |
| 0.062 | 0.125 | 90* | 0 | 50* | 20 | 40* | 0 | 0 | 10 | 60* | 0 | 0 | 0 | 0 | 0 |
| 0.125 | 0.03 | 50* | 20 | 60* | 40 | 100* | 30 | 20 | 30 | 100* | 0 | 30* | 0 | 20* | 0 |
| 0.125 | 0.062 | 85* | 20 | 80* | 40 | 60* | 30 | 30 | 30 | 90* | 0 | 50* | 0 | 30* | 0 |
| 0.125 | 0.125 | 100* | 20 | 98* | 40 | 100* | 30 | 100* | 30 | 100* | 0 | 60* | 0 | 95* | 0 |
| 0.25 | 0.03 | 95* | 65 | 98* | 65 | 100* | 40 | 100 | 60 | 100* | 0 | 60 | 65 | 90* | 60 |
| 0.25 | 0.062 | 100* | 65 | 98* | 65 | 100* | 40 | 100* | 60 | 100* | 0 | 65 | 65 | 95* | 60 |
| 0.25 | 0.125 | 100* | 65 | 100* | 65 | 100* | 40 | 100* | 60 | 100* | 0 | 70* | 65 | 100* | 60 |

*Synergistic effect shown.
Foxtail and watergrass were also treated, but both observed and expected results were 100% at each application rate, precluding evaluation of synergism.

EXAMPLE IV

This example represent a repeat of the test shown in Example III, except that the herbicides were applied one day after seeding, rather than on the same day. Only the annual ryegrass, shattercane, annual morning glory, yellow nutsedge, and wild oat weed species were used, and injury ratings on the emergent weeds were taken after three weeks. The results are shown in Table IV, where synergism is again evident.

TABLE IV
HERBICIDE SYNERGISM TEST RESULTS

Test Compounds:

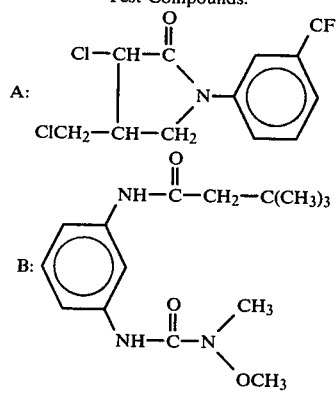

Applied to Soil One Day After Seeding
Percent Control - O: Observed E: Expected

| Application Rates (lb/A) | | Ryegrass | | Shatter-cane | | Morning glory | | Nutsedge | | Wild Oat | |
|---|---|---|---|---|---|---|---|---|---|---|---|
| A | B | O | E | O | E | O | E | O | E | O | E |
| Control Data: | | | | | | | | | | | |
| 0.062 | — | 0 | | 0 | | 0 | | 0 | | 0 | |
| 0.125 | — | 0 | | 0 | | 0 | | 0 | | 0 | |
| 0.25 | — | 40 | | 0 | | 0 | | 20 | | 0 | |
| — | 0.062 | 0 | | 0 | | 0 | | 0 | | 0 | |
| — | 0.125 | 0 | | 0 | | 0 | | 0 | | 0 | |
| — | 0.25 | 20 | | 0 | | 20 | | 0 | | 0 | |
| Test Data: | | | | | | | | | | | |
| 0.062 | 0.062 | 0 | 0 | 0 | 0 | 0 | 0 | 0 | 0 | 0 | 0 |
| 0.062 | 0.125 | 0 | 0 | 0 | 0 | 0 | 0 | 0 | 0 | 0 | 0 |
| 0.062 | 0.25 | 20 | 20 | 0 | 0 | 20 | 20 | 0 | 0 | 0 | 0 |
| 0.125 | 0.062 | 0 | 0 | 0 | 0 | 0 | 0 | 0 | 0 | 20* | 0 |
| 0.125 | 0.125 | 0 | 0 | 0 | 0 | 0 | 0 | 0 | 0 | 25* | 0 |
| 0.125 | 0.25 | 20 | 20 | 0 | 0 | 0 | 20 | 0 | 0 | 30* | 0 |
| 0.25 | 0.062 | 30 | 40 | 10* | 0 | 0 | 0 | 30* | 20 | 60* | 0 |
| 0.25 | 0.125 | 40 | 40 | 20* | 0 | 0 | 0 | 35* | 20 | 50* | 0 |
| 0.25 | 0.25 | 65* | 52 | 40* | 0 | 20 | 20 | 40* | 20 | 75* | 0 |

*Synergistic effect shown.

The compositions of this invention are useful as herbicides demonstrating synergistic activity for the control of undesirable vegetation. The compositions can be formulated in the same manner in which herbicides are generally formulated, and can be applied either separately or in combination. The compositions are applied to the locus where control is desired by any conventional method. The loci of application include soil, seeds, and seedlings, as well as established vegetation.

Formulations will generally contain one or more additives. Among these are inert ingredients and diluent carriers such as organic solvents, water, dust and granule carriers, and surface active, wetting, dispersing, and emulsifying agents. Fertilizers, such as ammonium nitrate, urea and superphosphate can also be included, as well as aids to rooting and growth, such as compost, manure, humus, sand, etc.

The most common formulations are dusts, wettable powders, granules, solutions and emulsifiable concentrates.

Dusts are free-flowing powder compositions containing the herbicidal compound impregnated on a particulate carrier. The particle size of the carrier is usually in the approximate range of 30 to 50 microns. Examples of suitable carriers are talc, bentonite, diatomaceous earth, and pyrophyllite. Anticaking and antistatic agents can be added, if desired. The composition generally contains up to 50% of active ingredient. Dusts, like liquid compositions can be applied by airplanes or ground spraying equipment.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols; salts of sulfonic acids; esters of long chain fatty acids; and polyhydric alcohols, in which the alcohol groups are free, omega-substituted polyethylene glycols of relatively long chain length.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

It is not necessary that the compositions be admixed with the soil particles. After application by the above discussed methods, they may be distributed below the soil surface to a depth of at least one-half inch by conventional means such as discing, dragging, or mixing.

What is claimed is:

1. A synergistic herbicidal composition consisting essentially of a mixture of
   (a) an effective amount of a pyrrolidone of the formula

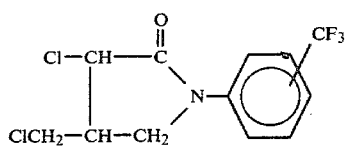

and
   (b) an effective amount of a urea of the formula

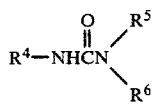

in which
   $R^4$ is p-chlorophenoxyphenyl;
   $R^5$ is $C_1-C_4$ alkyl; and
   $R^6$ is $C_1-C_4$ alkyl;
at a weight ratio of (a) to (b) of from about 0.5:1 to about 10:1.

2. A composition according to claim 1 in which the pyrrolidone is 1-m-trifluoromethylphenyl-3-chloro-4-chloromethyl-2-pyrrolidone.

3. A composition according to claim 1 in which the pyrrolidone is 1-m-trifluoromethylphenyl-3-chloro-4-chloromethyl-2-pyrrolidone and the urea is 3-[p-(p-chlorophenoxy)phenyl]1,1-dimethylurea.

4. A method of controlling undesirable vegetation which comprises applying to said vegetation an effective amount of a herbicidal composition consisting essentially of a mixture of
   (a) an effective amount of a pyrrolidone of the formula

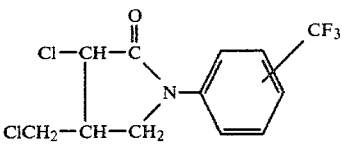

and
   (b) an effective amount of a urea of the formula

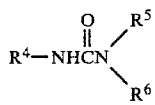

in which
   $R^4$ is p-chlorophenoxyphenyl;
   $R^5$ is $C_1-C_4$ alkyl; and
   $R^6$ is $C_1-C_4$ alkyl;
at a weight ratio of (a) to (b) of from about 0.5:1 to about 10:1.

5. A method according to claim 4 in which the pyrrolidone is 1-m-trifluoromethylphenyl-3-chloro-4-chloromethyl-2-pyrrolidone.

6. A method according to claim 4 in which the pyrrolidone is 1-m-trifluoromethylphenyl-3-chloro-4-chloromethyl-2-pyrrolidone and the urea is 3-[p-(p-chlorophenoxy)phenyl]1,1-dimethylurea.

* * * * *